United States Patent
Hummel et al.

(10) Patent No.: US 9,140,740 B2
(45) Date of Patent: Sep. 22, 2015

(54) SENSOR CHIP AND METHOD FOR MANUFACTURING A SENSOR CHIP

(71) Applicant: Sensirion AG, Stafa (CH)

(72) Inventors: Rene Hummel, Baar (CH); Ralph Steiner-Vanha, Hombrechtikon (CH); Ulrich Bartsch, Zurich (CH)

(73) Assignee: Sensirion AG, Stafa (CH)

( * ) Notice: Subject to any disclaimer, the term of this patent is extended or adjusted under 35 U.S.C. 154(b) by 0 days.

(21) Appl. No.: 14/099,153

(22) Filed: Dec. 6, 2013

(65) Prior Publication Data

US 2014/0159745 A1  Jun. 12, 2014

Related U.S. Application Data

(62) Division of application No. 13/597,630, filed on Aug. 29, 2012, now Pat. No. 8,633,047.

(30) Foreign Application Priority Data

Sep. 2, 2011 (EP) .................................. 11007137

(51) Int. Cl.
| | | |
|---|---|---|
| *G01R 27/26* | (2006.01) | |
| *G01N 27/22* | (2006.01) | |
| *H01L 23/522* | (2006.01) | |

(52) U.S. Cl.
CPC .......... *G01R 27/2605* (2013.01); *G01N 27/226* (2013.01); *H01L 23/5223* (2013.01)

(58) Field of Classification Search
CPC ............... G01R 27/26; G01R 27/2605; H01L 23/5223; G01N 27/226
USPC .............. 257/414, E21.001, E29.166; 438/29
See application file for complete search history.

(56) References Cited

U.S. PATENT DOCUMENTS

| | | |
|---|---|---|
| 4,347,550 A | 8/1982 | Rockliff |
| 4,429,343 A | 1/1984 | Freud |
| 4,564,882 A | 1/1986 | Baxter et al. |
| 4,651,121 A | 3/1987 | Furubayashi et al. |
| 4,728,882 A | 3/1988 | Stanbro et al. |
| 4,822,566 A | 4/1989 | Newman |
| 4,854,725 A | 8/1989 | Sims et al. |

(Continued)

FOREIGN PATENT DOCUMENTS

| | | |
|---|---|---|
| EP | 0483155 | 5/1992 |
| EP | 0911628 | 4/1999 |

(Continued)

OTHER PUBLICATIONS

Sensirion The Sensor Company, Introduction to Humidity—Basic Principles on Physics of Water Vapor, Version 2.0, Aug. 2009, pp. 1-6.

(Continued)

*Primary Examiner* — Selim Ahmed
(74) *Attorney, Agent, or Firm* — Cooper & Dunham LLP

(57) ABSTRACT

The present sensor chip comprises a substrate. A plurality of electrode elements is arranged at a first level on the substrate with at least one gap between neighboring electrode elements. A metal structure is arranged at a second level on the substrate, wherein the second level is different from the first level. The metal structure at least extends over an area of the second level that is defined by a projection of the at least one gap towards the second level.

7 Claims, 4 Drawing Sheets

(56) References Cited

U.S. PATENT DOCUMENTS

| | | | |
|---|---|---|---|
| 4,926,156 A | 5/1990 | Dickert et al. | |
| 4,935,207 A | 6/1990 | Stanbro et al. | |
| 5,028,906 A | 7/1991 | Moriya et al. | |
| 5,269,175 A | 12/1993 | Chmiel et al. | |
| 5,512,882 A | 4/1996 | Stetter et al. | |
| 5,653,939 A | 8/1997 | Hollis et al. | |
| 5,658,819 A | 8/1997 | Humphrey et al. | |
| 5,707,148 A | 1/1998 | Visser et al. | |
| 5,719,740 A | 2/1998 | Hayashi et al. | |
| 5,767,687 A | 6/1998 | Geist | |
| 5,837,886 A | 11/1998 | Nakahara et al. | |
| 5,840,255 A | 11/1998 | Kappel et al. | |
| 5,989,398 A | 11/1999 | Young et al. | |
| 6,191,593 B1 | 2/2001 | Tartagni et al. | |
| 6,249,130 B1 | 6/2001 | Greer | |
| 6,252,759 B1 | 6/2001 | Lange et al. | |
| 6,265,222 B1 | 7/2001 | DiMeo, Jr. et al. | |
| 6,326,228 B1 | 12/2001 | Hughes et al. | |
| 6,380,747 B1 | 4/2002 | Goldfine et al. | |
| 6,452,514 B1 | 9/2002 | Philipp | |
| 6,690,569 B1 | 2/2004 | Mayer et al. | |
| 7,795,056 B2 * | 9/2010 | Shih | 438/29 |
| 2002/0036507 A1 | 3/2002 | Kiesewetter et al. | |
| 2003/0094045 A1 | 5/2003 | Hamamoto et al. | |
| 2005/0013087 A1 * | 1/2005 | Wu et al. | 361/303 |
| 2007/0045690 A1 * | 3/2007 | Fukada | 257/295 |
| 2009/0267187 A1 | 10/2009 | Hose et al. | |
| 2011/0179861 A1 * | 7/2011 | Grange et al. | 73/335.04 |

FOREIGN PATENT DOCUMENTS

| | | |
|---|---|---|
| EP | 1607739 | 12/2005 |
| GB | 668196 | 3/1952 |
| GB | 2256489 | 12/1992 |
| JP | 54087292 | 7/1979 |
| JP | 64-016956 | 1/1989 |
| JP | 01300963 | 12/1989 |
| JP | 07020074 | 1/1995 |
| JP | 2010237130 | 10/2010 |
| WO | WO0231481 | 4/2002 |

OTHER PUBLICATIONS

C. Hagleltner et al., Smart Single-Chip Gas Sensor Microsystem, Nature 414, Nov. 15, 2001, pp. 293-296, ETH Zurich.

Delta-Sigma Modulation Sensor Interface Circuits with Improved Conversion Gain for Capacitive Readout Chemical Sensors, IEEJ Transactions on Sensors and Micromachines, 119(3), 138-142, Mar. 1, 1999.

Am Kummer et al., Tuning Sensitivity and Selectivity of Complementary Metal Oxide Semiconductor-Based Capacitive Chemical Microsensors, Anal Chem., May 1, 2004;76(9):2470-7.

Y.Y. Qui et al., A CMOS Humidity Sensor With On-Chip Calibration, Sensors and Actuators A: Physical, vol. 92, Issues 1-3, Aug. 1, 2001, pp. 80-87.

P. Van Gerwen et al., Nanoscaled Interdigitated Electrode Arrays for Biochemical Sensors, Conference Proceeding: DOI: 10.1109/SENSOR, Jul. 1997, 1997:635249ISBN: 0-7803-3829-4, In Proceeding of Solid State Sensors and Actuators, 1997, Transducers '97 Chicago, 1997 International Conference on, vol. 2.

Y. Sheiretov et al., Dielectrometry Measurements of Spatial Moisture Profiles in Oil-Impregnated Pressboard, Massachusetts Institute of Technology USA, Cambridge MA 02139.

* cited by examiner

SENSOR CHIP AND METHOD FOR MANUFACTURING A SENSOR CHIP

CROSS REFERENCE TO RELATED APPLICATIONS

This application is a divisional of U.S. Ser. No. 13/597,630, filed Aug. 29, 2012, which claims the priority of European application 11007137.0, filed Sep. 2, 2011, the entire contents of each of which is incorporated herein by reference in their entireties, as though fully set forth herein.

BACKGROUND OF THE INVENTION

The present invention relates to a sensor chip and a method for manufacturing a sensor chip.

Integrated fabrication techniques such as, for example, CMOS processing may be applied not only to manufacture electronic circuits but also to manufacture sensors, also denoted as sensor chips in the following. In such sensor chips, a sensor structure may be built in or on a substrate, such as a semiconductor substrate, and may or may not be integrated with associated electronic circuitry on the same chip.

In EP 1 236 038 B1, a capacitive sensor chip is disclosed containing multiple electrode elements structured on an oxide layer covering a substrate. The electrode elements are covered by insulating material which subsequently is etched. However, while the electrode elements may serve as an etch stop to the etching process, etching the insulating material in gaps between the electrode elements may only be controllable by defining the etching time upfront. This may result in varying depths etched into the insulating material. It was observed that the resulting etch depth may vary across a wafer e.g. with deeper etching results in the centre of the wafer than at its periphery. It was also observed that the resulting etch depth may vary from wafer to wafer.

In particular, when the gaps between the electrode elements will be filled by a measuring material acting, for example, as a dielectric layer between the respective electrode elements for capacitive measurements, a varying volume of the measuring material may impact the measurement results which effect may only be compensated by increased efforts in calibrating such sensor chips.

BRIEF SUMMARY OF THE INVENTION

According to a first aspect of the present invention a sensor chip is provided comprising a substrate, a plurality of electrode elements arranged at a first level on the substrate, at least one gap between neighbouring electrode elements, a metal structure arranged at a second level on the substrate, wherein the second level is different from the first level, wherein the metal structure at least extends over an area of the second level that is defined by a projection of the at least one gap towards the second level.

Preferred embodiments of the sensor chip may contain one or more of the following features:
the second level is arranged between the substrate and the first level;
the at least one gap is at least partly filled with a dielectric material of a measuring layer for building a capacitive sensor;
at least n electrode elements and n−1 gaps with n>2, wherein the n electrode elements represent n electrode fingers of at least one electrode structure, and in particular wherein the n electrode elements represent n electrode fingers of two interdigitating electrode structures;
the metal structure comprises multiple metal elements, and each metal element is assigned to one of the gaps for extending over an area of the second level that is defined by a projection of the assigned gap towards the second level;
each gap comprises at least an area in the first level confined by neighbouring electrode elements;
multiple of the electrode elements are arranged in parallel, and the at least one gap has the form of a rectangle;
the metal structure includes a single metal layer extending underneath each gap and the electrode elements;
at least part of the metal structure is used as an electrode structure for interacting with one or more of the electrode elements;
a protection layer covers the electrode elements and at least part of the metal structure, and comprises a measuring layer covering the protection layer;
the metal structure includes a shape complementary to a shape of the electrode elements in an area within outer electrode elements.

According to another aspect of the present invention, a method is provided for manufacturing a sensor chip, the sensor chip comprising a plurality of electrode elements arranged at a first level on a substrate, at least one gap between neighbouring electrode elements, and a metal structure arranged at a second level on the substrate, wherein the second level is different from the first level, and wherein the metal structure at least extends over an area of the second level that is defined by a projection of the at least one gap towards the second level, the method comprising the step of etching an insulating material covering the electrode elements and at least part of the metal structure and using the electrode elements and at least part of the metal structure as an etch stop.

Preferred embodiments of the method may contain one or more of the following features:
the insulating material is etched by means of an etchant applied for a predefined time;
a protection layer is applied to the electrode elements and at least the part of the metal structure, and a measuring layer is applied on top of the protection layer;
prior to etching the insulating material a first insulating layer is applied on the substrate and a first metal layer is applied to a layer stack comprising at least the first insulating layer and the substrate; the first metal layer is applied for building the metal structure, a second insulating layer is applied to the structured first metal layer, a second metal layer is applied to the second insulating layer, the second metal layer is structured for building the electrode elements, a third insulating layer is applied to the structured second metal layer, and the etching step is applied.

Other advantageous embodiments are listed in the dependent claims as well as in the description below.

The described embodiments similarly pertain to the sensor chip and the method. Synergetic effects may arise from different combinations of the embodiments although they might not be described in detail.

BRIEF DESCRIPTION OF THE DRAWINGS

The aspects defined above and further aspects, embodiments and advantages of the present invention can also be derived from the examples of embodiments to be described hereinafter with reference to the drawings. In the drawings, the figures show.

DETAILED DESCRIPTION OF THE INVENTION

Figure 1:
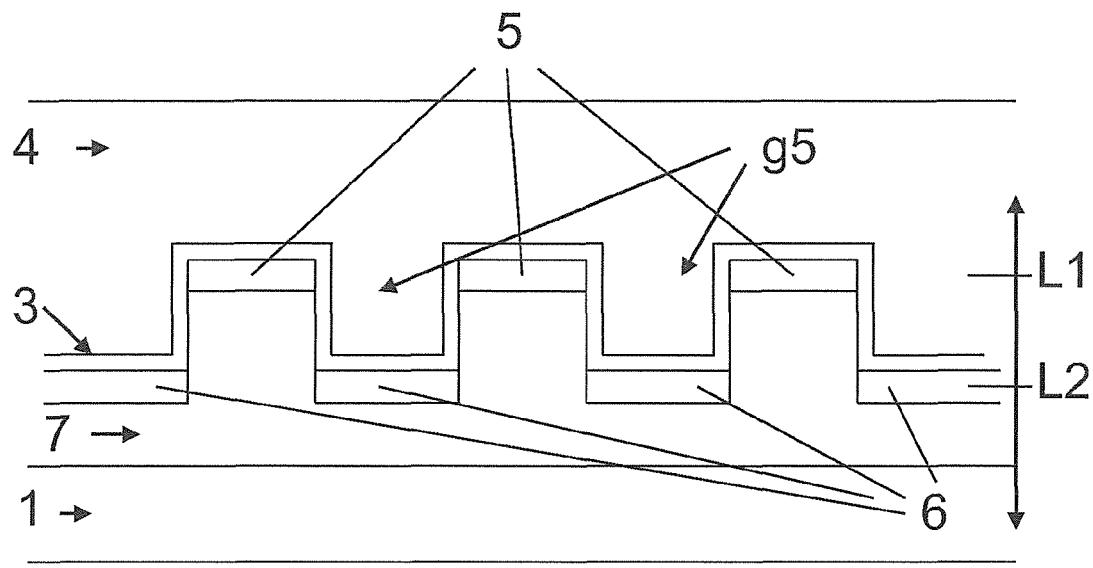
FIG. 1 a cross section of a sensor chip according to an embodiment of the present invention, FIG. 2 in diagrams (a) to (f) various stages in the manufacturing of a sensor chip in a cross sectional view according to an embodiment of the present invention, FIG. 3 a top view on the sensor chip as illustrated in FIG. 2(f), and FIG. 4 a top view on the sensor chip as illustrated in FIG. 2(f) with a different design of the metal structure, and FIG. 5 a cross section of a sensor chip according to another embodiment of the present invention.

A sensor chip according to an embodiment of the present invention provides a plurality of electrode elements arranged at a first level on the substrate with at least one gap between neighbouring electrode elements. A metal structure is arranged at a second level on the substrate, wherein the second level is different from the first level. The metal structure at least extends over an area of the second level that is defined by a projection of the at least one gap towards the second level.

In such sensor chip, the metal structure may act as an etch stop in addition to the electrode elements. The metal structure may preferably be applied in areas of the sensor chip, where with respect to a preferred direction of etching no electrode elements are present for serving as an etch stop. In a preferred embodiment, the metal structure may include a shape complementary to a shape of the electrode elements, at least in an area within outer electrode elements which area may impact the measurement. For example, when anisotropic etching is applied to a planar chip structure with an etching direction orthogonal to the planar chip structure towards the substrate, the etching of the sensor structures in etching direction may be stopped either by the electrode elements or by the metal structure in areas where no electrode elements are present in etching direction. Such areas may correspond to the gaps between electrode elements. Hence, in a preferred embodiment, the metal structure may be applied to all areas across the entire chip area where no electrode elements are present for serving as an etch stop in etching direction. In an alternate embodiment, the metal structure may only be applied to areas corresponding to gaps within outer electrode elements. In another embodiment, the metal structure may only be applied to confined areas corresponding to gaps between neighbouring electrode elements belonging to different interdigitating electrode structures. In another embodiment, the metal structure may be applied to all gaps existent, while in a different embodiment the metal structure may be embodied as a metal layer extending throughout the entire chip area. For defining an area the metal structure covers the or each gap defined by neighbouring electrode elements on the first level may preferably be projected onto the second level in etching direction. The area covered by the metal layer with respect to a projection of an assigned gap may actually include an area slightly smaller than the projected gap and still be covered by the present idea since such slightly smaller area may still satisfy the metal structure serving as an etch stop in case the etching process applied provides a recess with a rather low aspect ratio. Hence, it may be allowed that an area covered by the metal structure corresponding to an assigned gap may, for example, be at a maximum 10 percent smaller than the actual projection of the gap. Specifically, a width covered by the metal structure may be at a maximum 10 percent smaller than a width of the projected gap.

On the other hand, even if the aspect ratio of the recess achieved by the etching process applied is rather high, which means that the recess shows steep vertical walls between the first and the second level, it may be preferred that the area covered by the metal structure may extend at least a little beyond the projected area, and preferably may extend between 5 percent and 20 percent beyond the projected area. Specifically a width of the metal structure assigned to a gap may preferably extend the width of the gap projected by an amount between 5 percent and 20 percent. Such slightly oversized area of the metal structure may act as a safety margin in stopping the etching process in case the electrode elements and the metal structure are not ideally aligned with respect to each other.

Preferably, after having etched the insulating material and having exposed the electrode elements and the metal structure, in between the outer electrode elements there is no other material visible in a top view prior to applying additional layers than the electrode elements and the metal structure having served as etch stop. Generally, an electrode structure may be defined as structure comprising multiple electrode elements electrically connected with each other. Outer electrode elements may be defined as the electrode elements that constitute an outer boundary of an electrode arrangement comprising one or more electrode structures.

Typically, the electrode elements and the metal structure are deposited at different levels of stack that build the sensor chip. When applying an etchant to an insulating material into which the electrode elements and the metal structure are buried, the electrode elements may emerge first provided the first level is above the second level in etching direction, while the metal structure still is buried in the insulating material. When continuing etching, the remaining insulating material in the gaps between the electrode elements may be removed until the second etch stop in form of the metal structure emerges. The etching time may preferably be defined such that the element that is buried deepest into the insulating material in etching direction which in the present case is the metal structure will be uncovered by a sufficient likelihood. For example, an average etching time for uncovering the lower metal structure may be determined by etching samples. An applied etching time may be set to the average etching time plus a safety buffer in form of, for example, 10% to 25% of the average etching time.

As a result, a sensor chip may be generated with a uniform sensor structure, and specifically with a uniform depth of gaps between electrode elements, and specifically between electrode elements of interdigitating electrode structures, which gaps may be filled with measuring material.

It is noted that in the present application the term "applying a layer/material on a substrate/other layer" is not limited to directly depositing the layer/material on the substrate/other layer but shall also include a deposition onto any other layer as long as the layer/material is arranged above the substrate/other layer.

It is noted that the electrode elements may be understood as individual elements used as electrodes. Alternatively, electrode elements may be combined for building more complex electrode structures. In this respect, fingers of an interdigitating electrode may be understood as electrode elements, as may be a conductor electrically connecting the fingers in such interdigitating electrode structure. Electrode elements may belong to different electrode structures. For example, the electrode elements in form of fingers residing in the common first layer of the chip stack may belong to one or more, and preferably to two electrode structures.

Both, the electrode elements and the metal structure may be formed during a regular CMOS process each being formed in a dedicated metal layer. Preferably, the topmost metal layer in the resulting CMOS stack on the substrate may include the electrode elements while the metal structure may be arranged in the next layer underneath, or in any other layer further down in etching direction. In a preferred embodiment, the two topmost metal layers are used for building the electrode elements and the metal structure.

For a sensor chip according to any one of the described embodiments an etching step may be applied to an insulating material covering the electrode elements and at least part of the metal structure. The electrode elements and at least part of the metal structure is used as etch stop in this etching process. In this respect, the electrode elements and the metal structure are already built and buried in insulating material. The product resulting from this etching step may be an intermediate sensor chip with exposed electrode elements and at least parts of the metal structure being exposed. Such intermediate sensor chip may further be processed, for example, by applying a protection layer for preventing oxidation of the electrode elements, such as made out of silicon nitride, for example, and/or by applying a measuring layer which measuring layer may comprise a dielectric material which is susceptible to the chemical element or fluid to be measured. For example, the measuring layer may be embodied as a polymer layer susceptible to water which may change the dielectric properties of the measuring layer. Such change in turn can be detected as a change in capacity of the capacitive sensor chip. The final product, in this embodiment, may be a humidity sensor.

A preferred etching process to be applied is dry etching. However, in some scenarios wet etching can be applied, too.

Similar or relating components in the several figures are provided with the same reference numerals. The view in the figure is schematic and not fully scaled.

FIG. 1 shows a cross section of a sensor chip according to an embodiment of the present invention. The sensor chip comprises a substrate 1, for example a semiconductor substrate, which, in other embodiments, may be a glass or a ceramic substrate, and insulating material 7 on the substrate 1. At a first level L1 on the substrate 1, electrode elements 5 are provided having the form of electrode fingers belonging to two different interdigitating electrode structures realized in the first layer L1. At a second level L2 on the substrate 1, a metal structure 6 is provided comprising various metal elements. Both, electrode elements 5 as well as metal structure 6 are covered by a protective layer 3, for example in form of a silicon nitride coating. A measuring layer 4 is deposited on the protective layer 3. The measuring layer 4 preferably comprises a dielectric material between the electrode elements 5 and as such is arranged in gaps g5 between the electrode elements 5 and on top of the electrode elements 5 such that a capacitance between each two electrode elements 5 can be measured. Note that two neighbouring electrode elements 5 in the present arrangement are operated at different potentials, and accordingly belong to different electrode structures, i.e. to different interdigitating electrode structures. Note that the shape of the electrode elements 5 is not limited to electrode fingers but can take any shape desired such as concentric circles, etc. Specifically, two electrode structures may be built from concentric circle electrode elements in one embodiment.

FIG. 2 illustrates various stages in the manufacturing of a sensor chip. The diagrams in FIG. 2 may the manufacturing of an individual sensor chip or the manufacturing of a plurality of sensor chips on a common wafer from which wafer the individual sensor chips may finally be separated. For both alternatives, FIG. 2 may only show a section of an individual sensor chip or a section of a sensor chip on a common wafer.

Figure 2A:
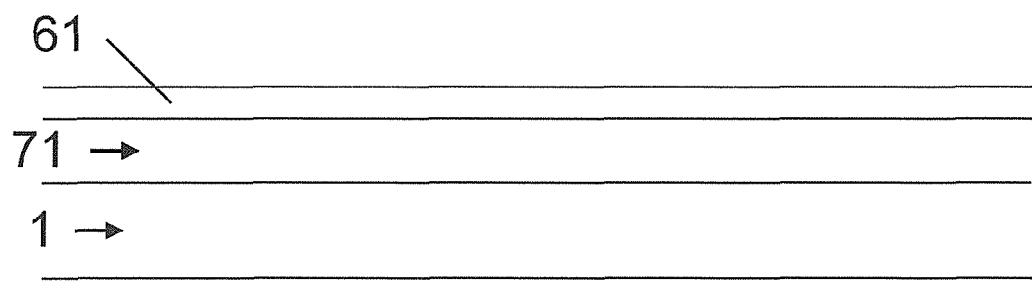
Figure 2B:
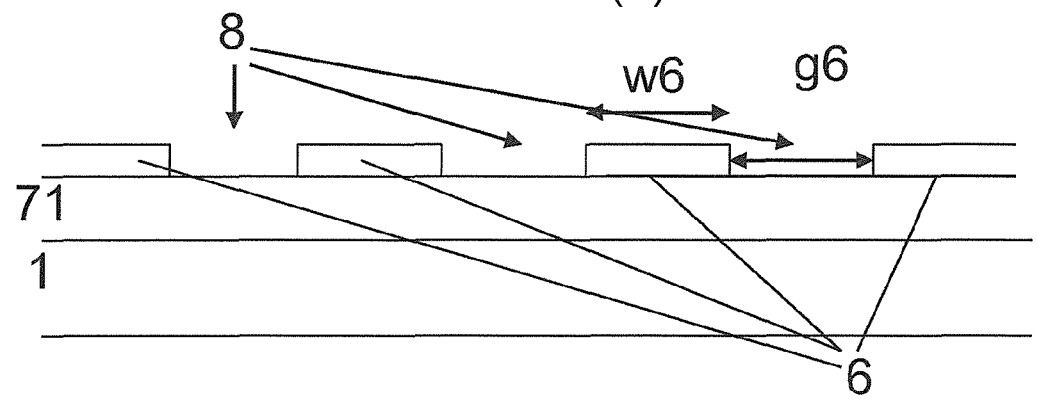

The stack in FIG. 2(a) may result from conventional CMOS processing: A first insulating layer 71, for example a silicon oxide layer, is deposited on a substrate 1. On top of the first insulating layer 71 a first metal layer 61 is arranged. In a following step, the first metal layer 61 is structured by conventional processes, such as wet etching or RIE (Reactive Ion Etching), for building a metal structure 6 from the first metal layer 61. The result is shown in FIG. 2(b). The metal structure 6 comprises metal elements arranged in parallel to each other which metal elements extend into the plane of projection. Each metal element has a width w6. Gaps 8 between two neighbouring metal elements show a width g6.

Figure 2C:
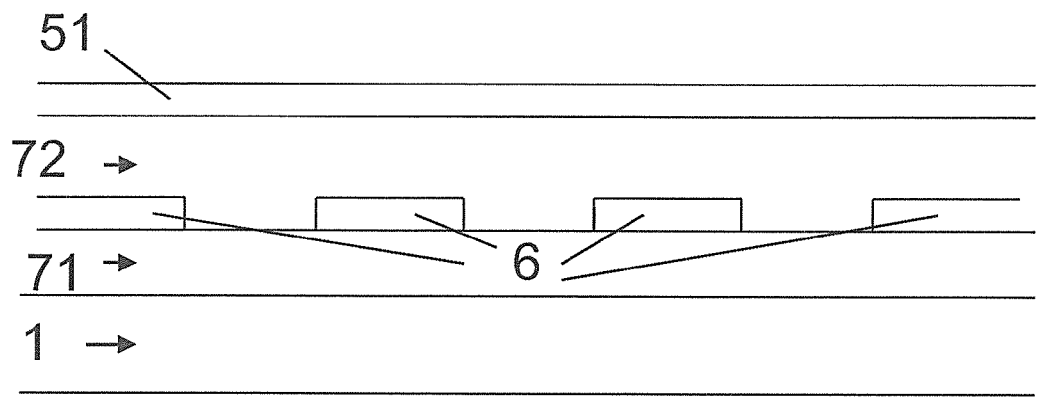
Figure 2D:
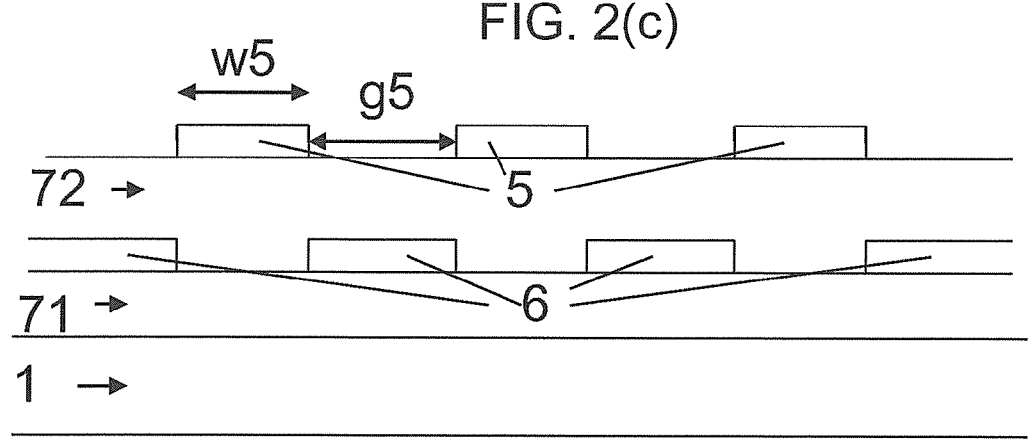

In a next step as shown in FIG. 2(c), a second insulating layer 72 is deposited on the metal structure 6. On top of the second insulating layer 72, which may be a silicon oxide layer in this embodiment, a second metal layer 51 is arranged. In a following step illustrated in FIG. 2(d), the second metal layer 51 is structured by conventional processes, such as wet etching or RIE (Reactive Ion Etching), for building electrode elements 5 from the second metal layer 51. The individual electrode elements 5 are arranged in parallel to each other extending into the plane of projection. Each electrode element 5 has a width w5. Gaps between two neighbouring electrode elements 5 show a width g5.

Figure 2E:
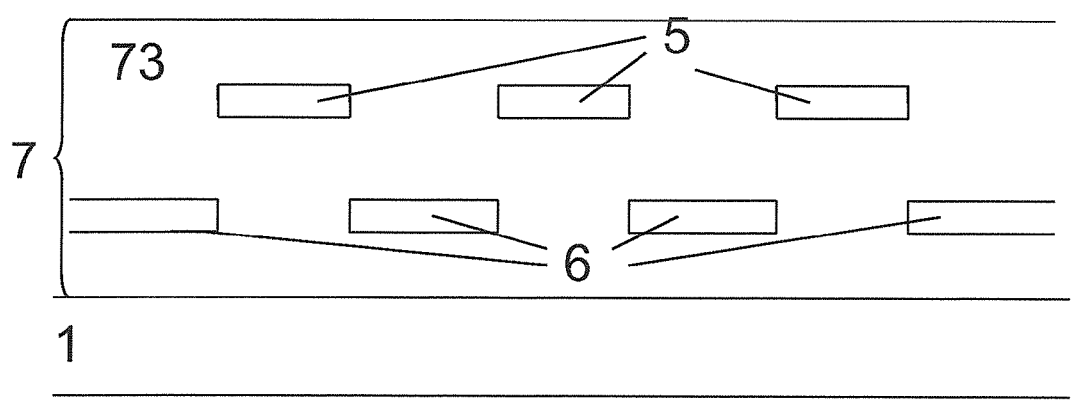

According to FIG. 2(e) a third electrically insulating layer 73, for example a silicon oxide layer, is deposited on the electrode elements 5. The entirety of insulating material present from the first, second and third insulating layers 71, 72 and 73 now is collectively denoted as insulating material 7. Note that after every depositing step an upper surface of such intermediate product may or may not be planarized.

Figure 2F:
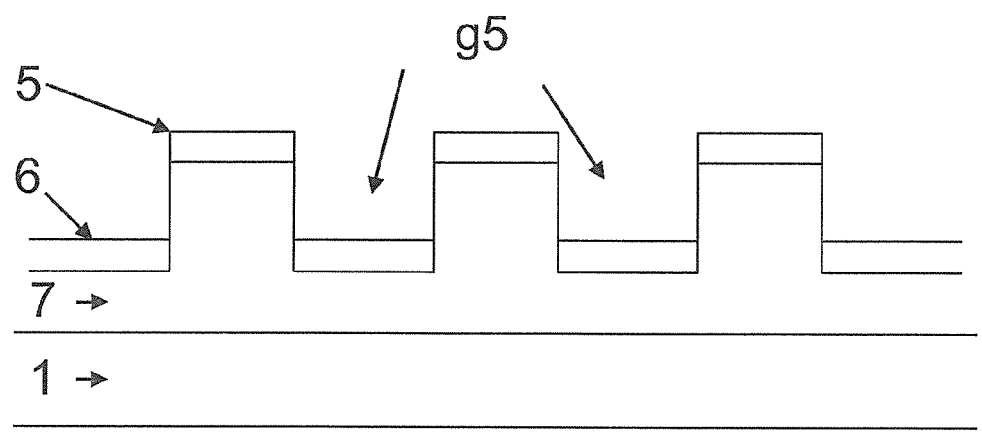

In a next step which is illustrated in FIG. 2(f), an etching step is applied for etching the insulating material 7 from the top for uncovering the electrode elements 5 and the metal structure 6. The etching step preferably is applied for a defined period in time which period in time is defined as being sufficient for reaching down to the metal structure 6 and exposing its metal elements. Both, the electrode elements 5 and the metal structure 6 act as an etch stop layer in the etching process. Hence, both, the electrode elements 5 and the metal structure 6 are made from a material suited for acting as an etch stop with respect to the etchant used. The etching step may include one of dry etching, wet etching, etc.

In a final step, the structure of FIG. 2(f) may be covered by a protection layer 3 and a measuring layer 4 resulting in a sensor chip according to FIG. 1.

Optionally, prior to the etching step as illustrated in FIG. 2(f), the third insulating layer 73 may be structured in order to prevent the following etching step from removing the insulating layer 73 from specific metal elements of the second metal layer 51 which elements shall serve as conventional conductive paths and which shall be protected from the outside by means of remaining portions of the third insulating layer 73.

Figure 3:
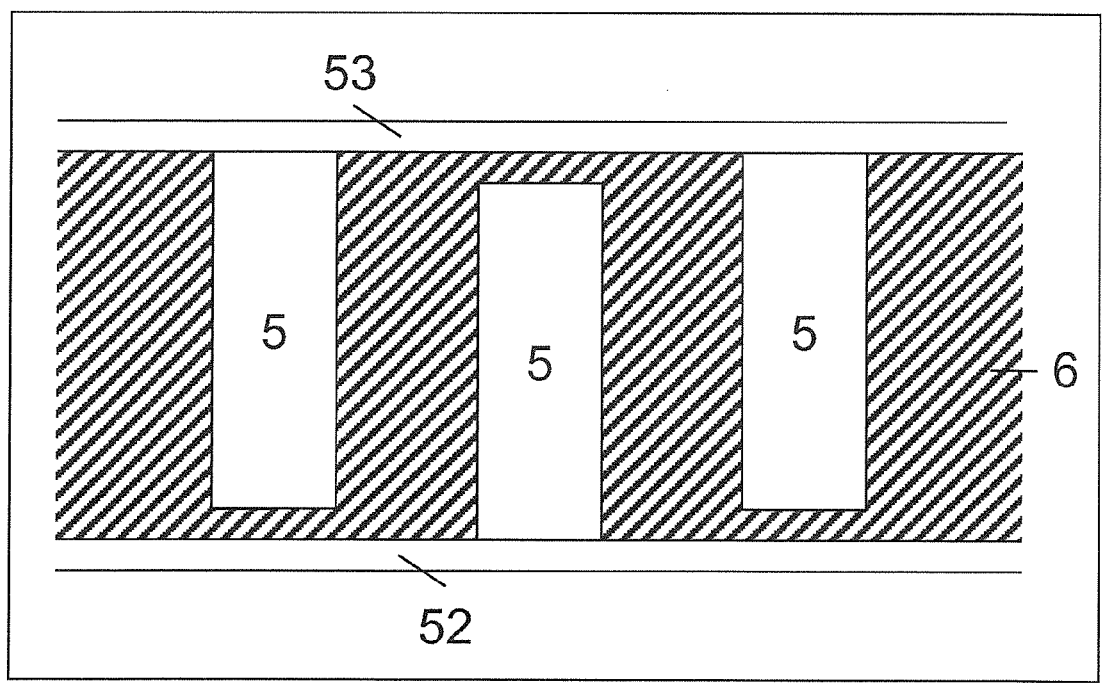

FIG. 3 illustrates a top view on the sensor chip of FIG. 2(f), i.e. before any protection layer 3 or measuring layer 4 is applied. FIG. 3 illustrates the electrode elements 5 as electrode fingers of two interdigitating electrode structures. Every second electrode element 5 is connected to electrode element 52 representing an electrical connection between these electrode elements 5. Each other second electrode element 5 is connected to electrode element 53 representing an electrical connection between these electrode elements 5. By applying different electrical potentials to the two interdigitating electrode structures a capacitive measurement may be conducted with the measuring layer 4 serving as dielectric filling between the two interdigitating electrode structures and on top of these. Whenever the measuring layer 4 is capable of accepting molecules from the environment, the present dielectric properties of the measuring layer 4 may be changed such that a presence and possibly a concentration of a chemical substance or a fluid in the environment may be determined. In case the measuring layer 4 is designed to accept water molecules from the environment, the sensor chip may work as a humidity sensor.

In FIG. 3, the shaded area illustrates the shape of metal structure 6 in top view. In the present example, the metal structure 6 is formed as a complement to the electrode elements 5 in an area within outer electrode elements 52, 53. Such complement design of the metal structure 6 is beneficial in that across the entire area between the outer electrode elements 52, 53 which simultaneously denotes the area which is relevant for the measurement, any unwanted unsteady etching is avoided for the reason that such entire area now is provided with an etch stop layer in form of the electrode elements 5 and the metal structure 6. A complement design of the metal structure 6 with respect to electrode elements 5 generally may at least comprise a metal structure 6 that at least extends over an area in the second level L2 that is defined by a projection of the at least one gap g5, and preferably all gaps g5, in the first level L1 towards the second level L2.

Figure 4:
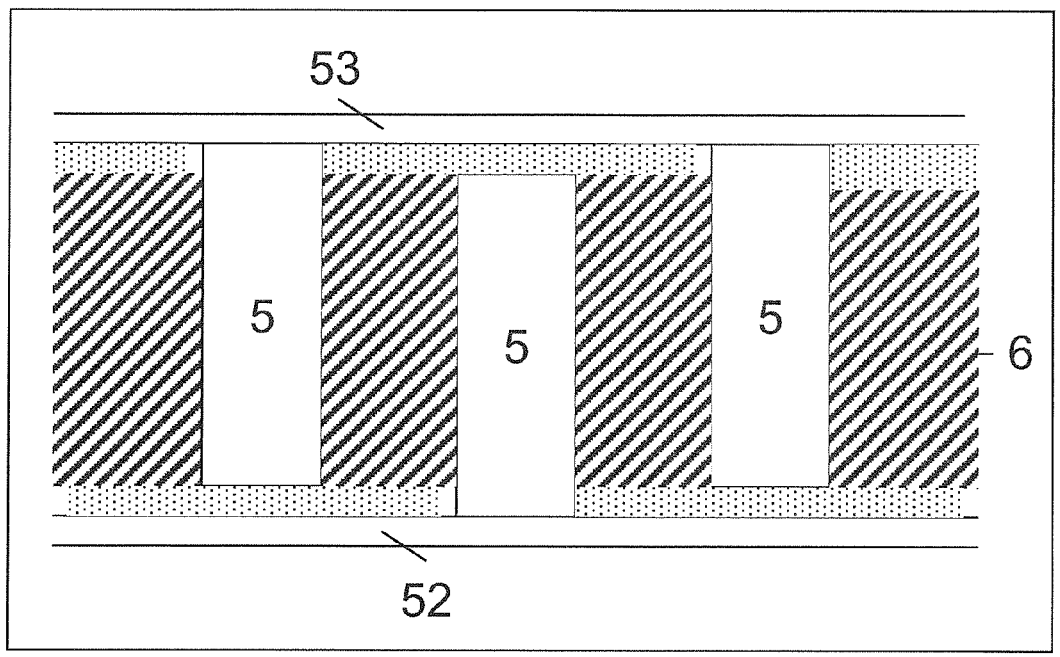

In FIG. 4 an alternate metal structure 6 is introduced. In a first approach, the metal structure 6 may only cover areas that are defined by the projection of gaps between neighbouring electrode elements 5 of different electrode structures. Such areas are illustrated by shaded rectangles. Such metal structure 6 may be sufficient for improving the measuring quality of the sensor chip. In an alternate embodiment, the metal structure 6 may additionally cover areas that are defined as a projection of gaps between neighbouring electrode elements 5 of the same electrode structure. Such areas are illustrated by dotted rectangles. In another embodiment, the metal structure 6 may be embodied, at least in an area between the outer electrode elements 52, 53 as a metal layer also extending underneath the electrode elements 5. In such embodiment, the structuring step according to FIG. 2(b) may be omitted or be limited to structures outside the relevant area.

In the above embodiments, electrode structures are solely formed by the electrode elements 5 in the first level L1, wherein preferably two interdigitating electrodes are formed by the electrode elements 5 by every second electrode element being interconnected and operated at a common electrical potential, and every other second electrode element being interconnected and operated at a different common electrical potential. The metal structure 6 may be operated at a floating potential. In another embodiment, the metal structure 6 itself may build one or more electrode structures, which are supplied with an electric potential. For example, the metal structure 6 may build another two interdigitating electrodes which may form a separate capacitive sensor on the second level L2, or may build a single electrode structure interacting with an electrode structure formed by all or selected electrode elements 5 from the first level L1, for example. In any such scenario, the metal elements may serve for both as an etch stop layer in the manufacturing of the sensor chip and as an electrode.

Note that any vertical measurement across levels of the stack in general may require at least two conducting layers at different levels in the stack. For example, in the sensor chip according to FIG. 1 a vertical measurement may be implemented, too. In addition to the above, further measurement scenarios can be envisaged: The electrode elements 5 in the first layer L1 may all be operated at a first electrical potential different from a second electrical potential at which all the metal elements in the second layers 6 are operated. In a different embodiment, the electrode elements 5 in the first level L1 may belong to two different interdigitating electrode structures for being operated at two different electrical potentials, wherein typically every second electrode element 5 is operated at the same first electrical potential while every second other electrode element 5 is operated at a same second electrical potential different from the first electrical potential. In such scenario, the metal elements in the second layer L2 may be operated at one of the following: The first potential, the second potential, a third potential being different from the first and the second electrical potential, and a combination of the first and the second potential applied to interdigitating electrodes built in the metal structure 6 of the second level L2.

Figure 5:
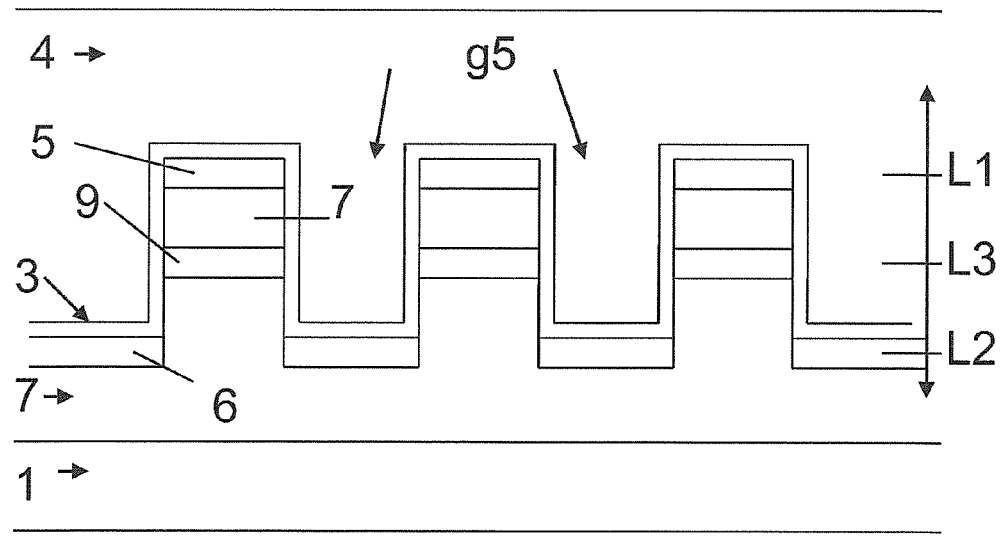

FIG. 5 shows a cross section of a sensor chip according to another embodiment of the present invention. In this example, the metal structure 6 may not be arranged in the neighbouring level to the electrode elements 5 residing in the first level L1. The metal structure 6 may be arranged more distant to the first level L1. In the present example, the metal structure 6 is arranged at a second level L2 while in a third level L3 between the first level L1 and the second level L2 additional electrode elements 9 may be arranged. In such embodiment, also vertical measurements across layers in the stack may be implemented.

In other embodiments, the layers used for building the metal structure 6 and the electrode elements 5 may not be the layers most close to the substrate 1 but instead may be the topmost metal layers in the CMOS process which, for example, may be the fifth and the sixth metal layer in the stack counted from the substrate 1.

While there are shown and described presently preferred embodiments of the invention, it is to be distinctly understood that the invention is not limited thereto but may be otherwise variously embodied and practised within the scope of the following claims.

The invention claimed is:

1. Sensor chip, comprising
a substrate,
a plurality of electrode elements arranged at a first level on the substrate,
a plurality of gaps between neighbouring electrode elements,
a metal structure arranged at a second level on the substrate, wherein the second level is different from the first level,
wherein the metal structure extends over areas of the second level that are defined by projections of the gaps towards the second level, and wherein the gaps are at least partly filled with a dielectric material of a measuring layer for building a capacitive sensor,
wherein the chip includes at least n electrode elements and n−1 gaps with n>2, wherein the n electrode elements represent n electrode fingers of at least one electrode structure, and in particular wherein the n electrode elements represent n electrode fingers of two interdigitating electrode structures,
wherein the metal structure comprises multiple metal elements, wherein each metal element is assigned to one of the gaps for extending over an area of the second level that is defined by a projection of the assigned gap towards the second level and wherein each metal element covers an area between 10 percent smaller and 20 percent larger than that defined by the projection of the gap to which it is assigned.

2. Sensor chip according to claim 1, wherein the second level is arranged between the substrate and the first level.

3. Sensor chip according to claim 1, wherein each gap comprises at least an area in the first level confined by neighbouring electrode elements.

4. Sensor chip according to claim 3, wherein multiple of the electrode elements are arranged in parallel, and wherein the at least one gap has the form of a rectangle.

5. Sensor chip according to claim 1, wherein at least part of the metal structure is used as an electrode structure for interacting with one or more of the electrode elements.

6. Sensor chip according to claim 1,
comprising a protection layer covering the electrode elements and at least part of the metal structure, and wherein the measuring layer covers the protection layer.

7. Sensor chip according to claim 1, wherein the metal structure includes a shape complementary to a shape of the electrode elements in an area within outer electrode elements.

* * * * *